(12) United States Patent
Tipler et al.

(10) Patent No.: US 7,709,267 B2
(45) Date of Patent: May 4, 2010

(54) SYSTEM AND METHOD FOR EXTRACTING HEADSPACE VAPOR

(75) Inventors: Andrew Tipler, Trumbull, CT (US); Christopher Mazza, Terryville, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 1075 days.

(21) Appl. No.: 11/251,310

(22) Filed: Oct. 14, 2005

(65) Prior Publication Data

US 2006/0099718 A1    May 11, 2006

Related U.S. Application Data

(63) Continuation of application No. PCT/US2004/011487, filed on Apr. 14, 2004.

(60) Provisional application No. 60/462,731, filed on Apr. 14, 2003, provisional application No. 60/481,558, filed on Oct. 24, 2003.

(51) Int. Cl.
*G01N 30/24* (2006.01)
*G01N 1/22* (2006.01)
*G01N 35/10* (2006.01)
*G01N 30/02* (2006.01)
*G01N 30/08* (2006.01)

(52) U.S. Cl. .................... 436/178; 73/19.02; 73/23.41; 73/23.42; 73/863.01; 73/863.02; 73/863.03; 73/863.11; 73/864.21; 422/68.1; 422/83; 422/88; 422/89; 436/43; 436/161; 436/177; 436/181

(58) Field of Classification Search ..... 73/19.01–19.02, 73/23.41–23.42, 863.01–863.03, 863.11–863.12, 73/864.21; 422/68.1, 83, 88–89; 436/43, 436/161, 177–178, 181
See application file for complete search history.

(56) References Cited

U.S. PATENT DOCUMENTS 3,120,749 A * 2/1964 Paglis et al. ................. 73/23.24
3,545,279 A * 12/1970 Jentzsch et al. .......... 73/863.81

(Continued)

FOREIGN PATENT DOCUMENTS

SU          1723516      *    3/1992

OTHER PUBLICATIONS

Keen, E. F. et al, Journal of Scientific Instruments 1956, 33, 449-450.*

(Continued)

*Primary Examiner*—Arlen Soderquist
(74) *Attorney, Agent, or Firm*—St. Onge Stewart Johnston & Reens LLC (57) ABSTRACT

A system and method for extracting headspace vapor is generally disclosed comprising pressurizing a vessel containing headspace vapor with a carrier gas and subsequently venting the sample mixture through an adsorbent trap and out a vent. A flow controller is employed to gradually increase the flow therethrough as the pressure drops as a result of the gradual depletion of headspace vapor in the vessel and, in certain embodiments, the flow controller maintains a constant flow rate. Due to the time saved, in some embodiments, multiple pressurization-venting cycles are implemented to maximize the amount of vapor extracted from the vial. Due to the constant flow rate, in certain embodiments, the pressure decay is monitored and compared to reference values in order to determine whether the sample vessel has a leak or other defect.

27 Claims, 7 Drawing Sheets

U.S. PATENT DOCUMENTS

| | | | | |
|---|---|---|---|---|
| 4,180,389 A | * | 12/1979 | Paul | 95/11 |
| 4,199,988 A | * | 4/1980 | Riegger | 73/863.81 |
| 4,464,940 A | | 8/1984 | Pospisil | 73/864.21 |
| 4,476,733 A | * | 10/1984 | Chlosta et al. | 73/863.91 |
| 4,484,483 A | | 11/1984 | Riegger et al. | 73/864.23 |
| 4,489,593 A | * | 12/1984 | Pieters et al. | 73/38 |
| 5,363,707 A | * | 11/1994 | Augenblick et al. | 73/864.84 |
| 5,441,700 A | * | 8/1995 | Markelov | 422/83 |
| 5,545,252 A | | 8/1996 | Hinshaw et al. | 95/15 |
| 5,711,786 A | | 1/1998 | Hinshaw | 95/82 |
| 5,720,798 A | * | 2/1998 | Nickerson et al. | 96/102 |
| 5,792,423 A | | 8/1998 | Markelov | 422/83 |
| 5,932,482 A | | 8/1999 | Markelov | 436/181 |
| 5,998,217 A | * | 12/1999 | Rao et al. | 436/179 |
| 6,146,895 A | * | 11/2000 | Green et al. | 436/47 |
| 6,395,560 B1 | | 5/2002 | Markelov | 436/181 |
| 6,652,625 B1 | | 11/2003 | Tipler et al. | 95/82 |
| 7,219,532 B2 | * | 5/2007 | Tipler et al. | 73/23.42 |
| 7,468,095 B2 | * | 12/2008 | Tipler et al. | 95/82 |

OTHER PUBLICATIONS

Drozd, J. et al, Chromatographia 1982, 16, 309-311.*
Kolb, B., Analytical Chemistry Symposia Series 1984, 20, 119-126.*
Schoene, K. et al, Fresenius' Zeitschrift fuer Analytische Chemie 1984, 319, 903-906.*
Petri, H.-M. et al, Macromolecules 1994, 27, 2714-2718.*
Wessels, P. et al, LC-GC 1995, 13, 480,482,484.*
Elmore, J. S. et al, ACS Symposium Series 1998, 705, 69-77.*
Miller, M. E. et al, LC-GC 2000, 18, 968,970,972-975.*
Ettre, L. S., Advances in Experimental Medicine and Biology 2001, 488, 9-32.*
Li, Z. et al, Journal of Pharmaceutical and Biomedical Analysis 2002, 28, 673-682.*
Javier Tabera, et al. "Optimization of Dynamic Headspace Sampling for the Analysis of Trace Volatile Components of Grape Juice: Use of PTV Injector for Intermediate Trapping" (Journal of High Resolution Chromatography vol. 14, Jun. 1991, 6 pages).
Alberto J. Nunez, et al. "Pre-Concentration of Headspace Volatiles for Trace Organic Analysis by Gas Chromatography" (Elsevier Science Publishers B.V. Amsterdam, NL, vol. 300 1984, 37 pages).

* cited by examiner

SYSTEM AND METHOD FOR EXTRACTING HEADSPACE VAPOR

PRIOR APPLICATIONS

This application is a continuation of International Patent Application No. PCT/US2004/011487 filed on Apr. 14, 2004, which designates the United States and claims priority of U.S. Provisional Patent Application Nos. 60/462,731 filed on Apr. 14, 2003 and 60/481,558 filed on Oct. 24, 2003.

FIELD OF THE INVENTION

The present invention relates to a system and method for extracting headspace vapor from a vessel. More specifically, the invention relates to a system and method for maximizing the amount of vapor extracted by maintaining a constant flow as the pressure inside the vessel decreases.

BACKGROUND OF THE INVENTION

Chromatography is essentially a physical method of separation in which constituents of a test sample in a carrier gas or liquid are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various elements of the sample—which differ based upon differences among distribution coefficients of the elements—cause the sample to be separated into the respective elements. At the end of the column, the individual components are more or less separated in time. Detection of the gas provides a time-scaled pattern, typically called a chromatogram, that, by calibration or comparison with known samples, indicates the constituents of the test sample. An example of the process by which this occurs is described in U.S. Pat. No. 5,545,252 to Hinshaw.

Often, the sample is first obtained using a sampling device, which subsequently transfers the sample to the chromatograph. One means of obtaining a sample and introducing it into a chromatographic column is known as "headspace sampling." In conventional headspace sampling, sample material is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the chromatographic column in such a way as to allow for the transfer of a portion of the vial gas phase into the column for a short period of time. An example of such a sampling device is disclosed in U.S. Pat. No. 4,484,483 to Riegger et. al. An example of a chromatographic system employing such a sampling device is disclosed in U.S. Pat. No. 5,711,786 to Hinshaw, which describes using a chromatographic injector between the vial and the chromatographic column.

Typically, it is desired to pre-concentrate the analytes in the sample, and occasionally, remove moisture therefrom, prior to introducing the sample into the chromatographic column. Accordingly, as disclosed in U.S. Pat. Nos. 5,792,423 and 6,395,560 to Markelov, these systems will typically include some kind of "trap" for this purpose, which retains the analytes as they are carried through the trap, and which are later released from the trap, usually by heating, and swept into the chromatographic column.

Though various types of traps have been suggested, one particularly advantageous way to perform this pre-concentration (and possible moisture removal) prior to introducing the sample into a chromatographic column is through the use of an adsorbent trap. These traps, which adsorb the analytes and then subsequently desorbed those analytes, do not suffer from the same slow flow rates as on-line traps (such as cryogenic traps) that result from the impedance of the column. When using an adsorbent trap, a carrier gas can be used to first pressurize the vial and then, after pressurization, to carry the sample vapor through the trap, which will adsorb the analytes to be measured, and then vent out of the system, which is the simplest way to extract vapor from a vessel. Accordingly, numerous arrangements employing an adsorbent trap have been employed for the purpose of pre-concentrating the analytes of a sample extracted by a sampling device such as a headspace sampler. Examples of such arrangements are disclosed in U.S. Pat. No. 5,932,482 to Markelov and U.S. Pat. No. 6,652,625 to Tipler.

However, these systems typically suffer from several disadvantages. One problem is that the process is slow. This is due to the fact that the pressure in the vial is proportional to the amount of sample in the vial. Therefore, as the sample vapor elutes from the vial, the pressure drops. Accordingly, the rate of flow decreases, resulting in undesirable vent times. Indeed, trials have shown that a 22 mL vial pressurized to 40 psig with helium can take longer than five minutes to effect a full extraction, even with high initial flow rates.

Another problem with current systems is that, in order to maximize performance with respect to resolution, sensitivity and inertness, it is generally desired to use capillary columns for chromatography. However, with capillary columns, the carrier gas flow rates will be low, so direct injection of large quantities of vapor is not possible. For example, an injection volume of about 100 μL is typical. A typical headspace sample vial, however, usually has a capacity of about 22 mL, with a maximum sample volume about half that. Therefore, only about 1% of the total headspace vapor is actually injected into the column. Accordingly, system sensitivity can be increased nearly 100× over current headspace sampling systems by increasing the percentage of the available headspace vapor that is actually injected into the column. This is particularly useful for applications requiring very low detection limits, such as environmental and other trace-level analysis of Volatile Organic Compounds (VOCs) in a variety of sample matrices.

Yet another problem with current systems is that a headspace sampler is typically used to test a number of large number vials in sequence, and occasionally, a vial may have a leak or for some other reason may not contain the proper amount of sample, leading to erroneous analytical data. Accordingly, it is advantageous to review the pressure decay profiles for these vials—i.e. in the decay in pressure as a function of time. However, as previously mentioned, the pressure in the vial is proportional to the amount of sample present, and thus, a plot of pressure decay as a function of time results in exponential, rather than linear, profiles, making a determination of whether the rate of decay is appropriate difficult.

What is desired, therefore, is a system and method for extracting headspace vapor that reduces the time required to vent fluid through a trap. What is further desired is a system and method for extracting headspace vapor that increases the amount of sample vapor that is actually injected into a chromatographic column. What is also desired is a system and method for extracting headspace vapor that increases the ability to check for leaks in the sample vials and verify that the proper amount of sample is present therein.

SUMMARY OF THE INVENTION

Accordingly, an object of the present invention is to provide a system and method for extracting headspace vapor that prevents the rate of flow through a trap from decreasing as the sample elutes from a headspace vial.

It is a further object of the present invention to provide a system and method for extracting headspace vapor that effectively extracts residual sample vapor remaining in the vial after an initial extraction.

It is yet another object of the present invention to provide a system and method for extracting headspace vapor that produces linear pressure decay profiles to facilitate checking for leaks in headspace vials and the presence of proper sample amounts.

To overcome the deficiencies of the prior art and to achieve at least some of the objects and advantages listed, the invention comprises a method of extracting headspace vapor, including providing a vessel holding headspace vapor containing analytes to be measured, inserting a receptacle into the vessel, pressurizing the vessel by communicating carrier gas from a carrier gas inlet through the receptacle and into the vessel, venting the headspace vapor and carrier gas in the vessel through an adsorbent, which adsorbs analytes in the headspace vapor, and out a vent, and controlling the flow of the carrier gas carrying the headspace vapor as it is vented such that the rate of flow is increased as the rate of flow decreases due to the depletion of headspace vapor in the vessel.

In some of these embodiments, the invention comprises a method for extracting headspace vapor including repeating the steps of pressurizing and venting a predetermined number of times.

In certain embodiments, the invention comprises a method for extracting headspace vapor including monitoring the pressure in the vessel as headspace vapor is vented from the system.

In another embodiment, the invention comprises a system for extracting headspace vapor, including a vessel for holding headspace vapor containing analytes to be measured, a receptacle adapted to be inserted and withdrawn from the vessel, the receptacle having a vessel port, a carrier gas inlet for supplying carrier gas to pressurize the vessel and to carry the headspace vapor, an adsorbent housing in fluid communication with the carrier gas inlet, the adsorbent housing having an adsorbent disposed therein for adsorbing the analytes in the carrier gas carrying the headspace vapor, a vent in fluid communication with the adsorbent housing for venting the carrier gas carrying the headspace vapor, wherein, when the vessel port of the receptacle is in fluid communication with the vessel and the carrier gas inlet is open, carrier gas flows into and pressurizes the vessel, wherein, when the vessel port of the receptacle is in fluid communication with the vessel and the carrier gas inlet is closed, the headspace vapor and carrier gas flow into the adsorbent housing and are vented through the vent, and a flow controller in fluid communication with the adsorbent housing and the vent for increasing the rate of flow of the carrier gas carrying the headspace vapor as the rate of flow decreases due to depletion of the headspace vapor in the vessel.

In some of these embodiments, the invention comprises a system for extracting headspace vapor including processor for receiving data and generating a signal causing the steps of pressurizing and venting to be performed multiple times.

In certain embodiments, the invention comprises a system for extracting headspace vapor including a gauge for monitoring the pressure in the vessel as headspace vapor is vented from the system.

DETAILED DESCRIPTION OF THE DRAWINGS

Figure 1:
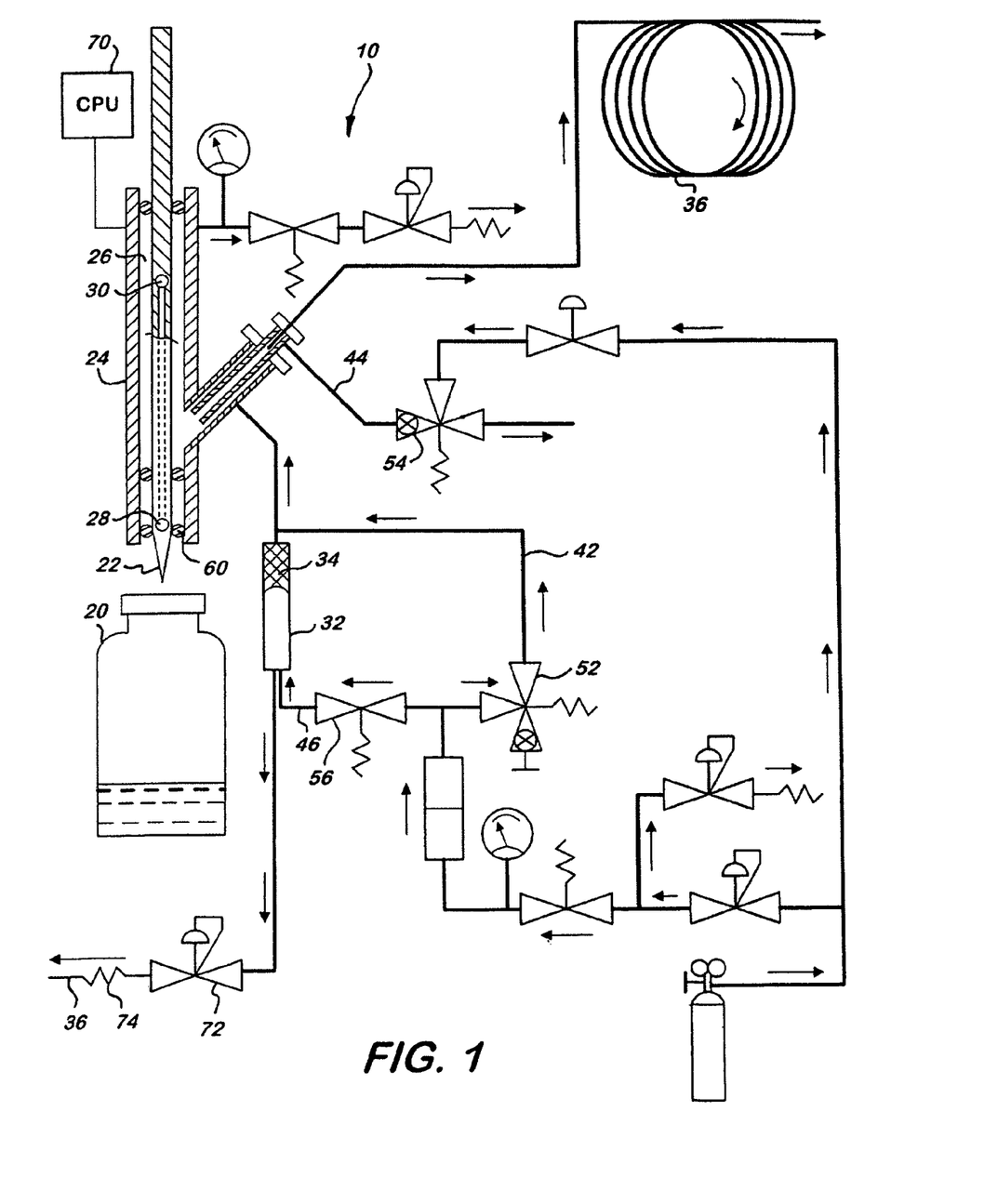
FIG. 1 is a schematic view of a system for extracting headspace vapor in accordance with invention in standby mode.

The basic components of one embodiment of a system for extracting headspace vapor 10 in accordance with the invention are illustrated in FIG. 1. As used in the description, the terms "top," "bottom," "above," "below," "over," "under," "on top," "underneath," "up," "down," "upper," "lower," "front," "rear," "forward" and "back" refer to the objects referenced when in the orientation illustrated in the drawings, which orientation is not necessary for achieving the objects of the invention.

As illustrated in FIG. 1, which shows the system 10 in standby mode, a sampling device, such as a headspace sampler, holds a plurality of vessels (i.e., headspace vials) 20 that contain the sample to be extracted and analyzed. Typically, the headspace sampler includes a sampling needle 22 disposed in a sampling head 24, and the needle 22 is adapted to be inserted and withdrawn from the vessels 20. The sampling head 24 has a sample chamber 26, and the sampling needle 22 has a vessel port 28 through which fluid is communicated between the needle 22 and the interior of the vials 20 and a sample chamber port 30 through which fluid is communicated between the needle 22 the sample chamber 26.

An adsorbent housing 32 having an adsorbent 34 disposed therein (commonly referred to as an adsorbent trap), a flow controller 72, a fixed restrictor 74, and a vent 36 are in fluid communication with the sample chamber 26. Accordingly, when headspace vapor is extracted from a vial 20 and mixes with a carrier gas, this sample mixture can flow through the adsorbent 34, which will adsorb the analytes to be measured, and out the vent 36 to the atmosphere. In certain advantageous embodiments, the adsorbent 34 is hydrophobic, thereby allowing moisture to be easily purged from the system by carrier gas, as further explained below. The adsorbent 34 may include any material suitable for this purpose, such as, for example, graphitized carbon black, a polymeric adsorbent, or a carbon molecular sieve.

The adsorbent housing 32 is in fluid communication with a gas chromatograph, the basic components of which are a chromatographic column 36 and a detector (not shown). Accordingly, analytes that have been adsorbed by the adsorbent 34 can be desorbed into the column 36. For this reason, in certain advantageous embodiments, the adsorbent housing 32 is temperature controllable, and thus, the adsorbent 34 can be heated to desorb the analytes retained by the adsorbent 34 before a carrier gas sweeps them out of the housing 32 and into the column 36.

A plurality of gas inlets are provided to supply and control fluid flowing throughout the system 10. For example, the system includes a first carrier gas inlet 42 for generally providing carrier gas needed by the system. For instance, the inlet 42 may provide carrier gas to different parts of the system 10 at different stages of operation, such as, for example, by providing the sampling head 24 with fluid to pressurize the vessel 20, or, as another example, by providing carrier gas to the adsorbent housing 32 to carry a sample containing analytes thereto or to sweep away moisture contained therein. The system 10 also has a second gas inlet 44 for providing gas that may be used by various parts of the system at various stages, but primarily for isolating the chromatographic column 36 from the rest of the system in order to prevent contaminated fluid from entering the column 36 until it is specifically desired to desorb the analytes thereinto. The system also includes a third inlet 46, primarily for providing carrier gas to the adsorbent housing 32 in order to sweep analytes into the column 36 as the analytes are desorbed from the adsorbent 34. Valves 52, 54, 56 are provided to open and close inlets 42, 44, 46, respectively.

Figure 2:
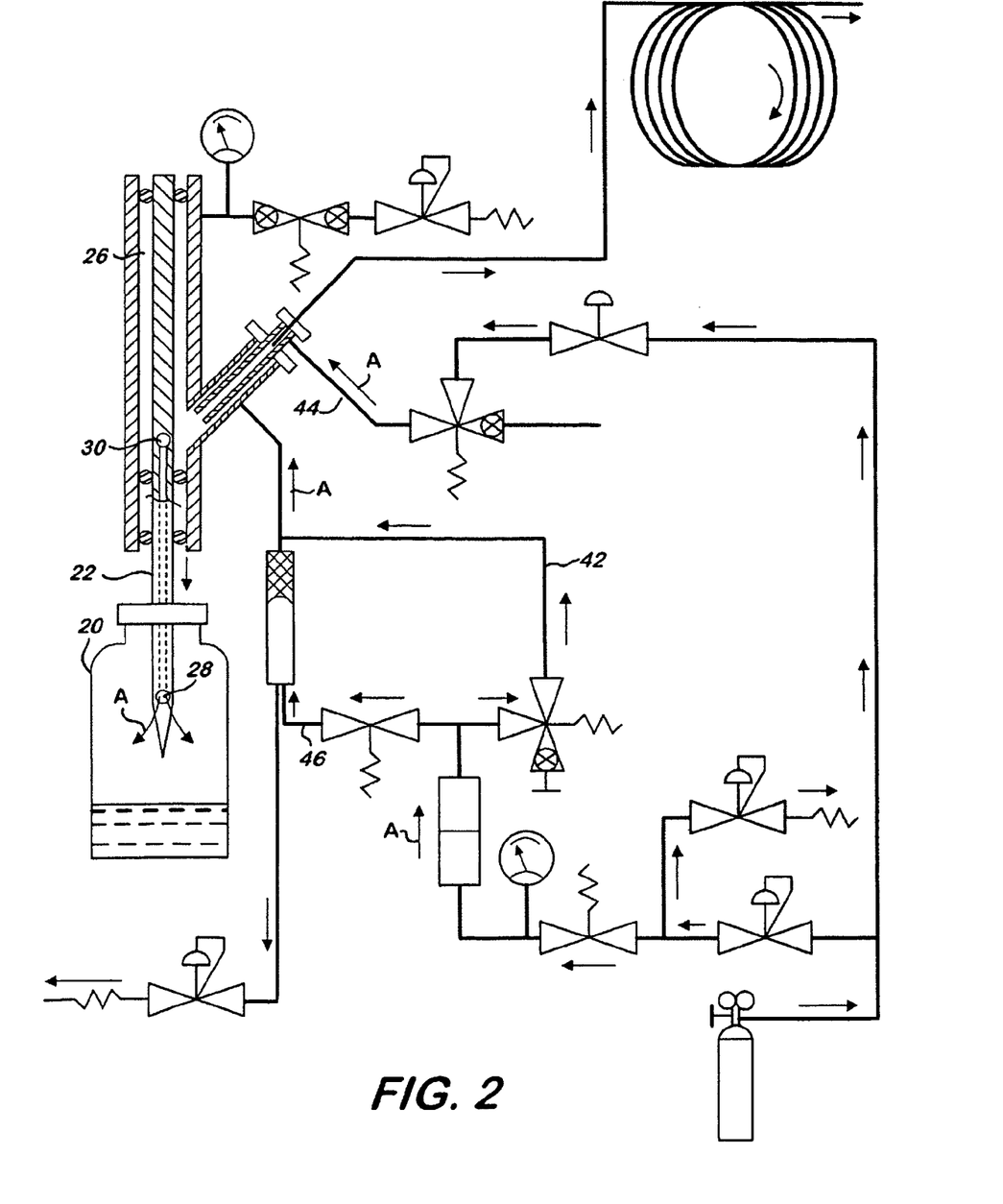
FIG. 2 is a schematic view of the system for extracting headspace vapor of FIG. 1 during the vial pressurization stage.

Operation of the above described assembly is illustrated stepwise FIGS. 2-7. A pressurization step is illustrated in FIG. 2. As shown therein, the sampling needle 22 descends into the vial 20, bringing the vessel port 28 into fluid communication with the interior of the vial 20. The inlets 42, 44, 46 are all opened, sending fluid into the sample chamber 26, through the chamber port 30, down through the needle 22, and into the vial 20 (indicated by arrows A). In this way, the vial is pressurized.

Figure 3:
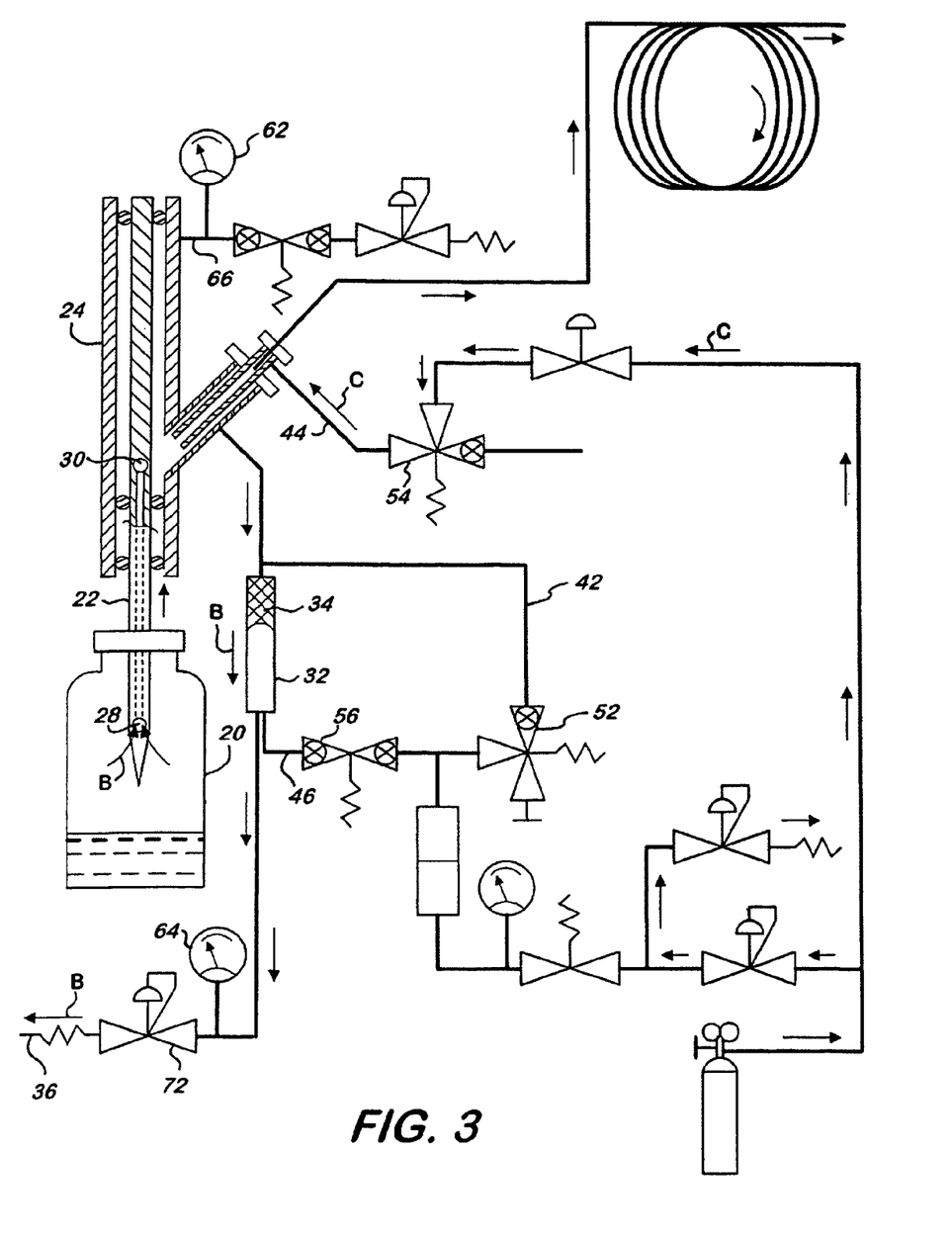
FIG. 3 is a schematic view of the system for extracting headspace vapor of FIG. 1 during the venting (trap load) stage.

A venting (or trap load) step is illustrated in FIG. 3. As shown therein, the inlet valve 52 is closed, terminating the supply of fluid from the inlet 42. Likewise, the valve 56 terminates the supply of fluid from inlet 46. As a result, fluid containing the analytes to be measured elutes from the vial 20 through the vessel port 28, through the needle 22, out the chamber port 30, through the adsorbent housing 32, where the adsorbent 34 adsorbs the analytes, and out through the vent 36. (indicated by arrows B). The inlet valve 54 remains open, allowing fluid to continue to enter through the inlet 44 and isolate the column 36 (indicated by arrows C).

Because the pressure in the vial 20 is proportional to the amount of sample in the vial 20, the pressure drops as the headspace vapor elutes from the vial 20, which normally causes the rate of flow to gradually decrease during the venting process. To counter this result, the flow controller 72, in response to the gradual decrease in pressure, gradually increases the flow therethrough, effectively increasing the rate of flow as the depletion of the headspace vapor in the vial 20 decreases the rate of flow. In certain advantageous embodiments, the flow controller 72 is configured to increase flow in an amount directly proportional to the decrease in pressure, thereby maintaining a constant flow rate. In this way, the process of extracting headspace vapor from the vial 20 does not immediately begin gradually slowing down as the venting stage proceeds, thereby resulting in quicker extraction times.

In some embodiments, the flow controller 72 comprises a forward pressure regulator. However, in other embodiments, the flow controller may comprises any device suitable for controlling flow therethrough, such as, for example, a mass flow controller or an electronic flow controller.

The aforementioned steps of pressurizing the sample vial 20 and venting the headspace therein through the adsorbent housing 32 and out the vent 36, however, does not extract all of the headspace from the vial 20. Instead, a certain percentage of the original headspace vapor remains in the vial 20 at atmospheric pressure. This residual vapor remaining in the vial 20 after the initial pressurization and venting is represented by the following equation:

$$R = 100 \cdot \left(\frac{P_{lo}}{P_{hi}}\right) \quad (1)$$

where R is the residual vapor (percentage of original headspace vapor) remaining in the vial, $P_{lo}$ is the absolute pressure (normally, atmospheric) after venting through the adsorbent housing 32 has occurred, and $P_{hi}$ is the absolute pressure (elevated) before venting through the adsorbent housing 32 has occurred.

While increasing the value of Phi or reducing the value of Plo would increase the amount of vapor extracted, a more practical way of reducing the value of R (i.e., increasing the amount of vapor extracted) is by performing multiple pressurization/venting cycles. Because the amount of time expended to perform a pressurization-venting cycle is significantly decreased due to the use of the flow controller 72 to maintain a constant flow rate, it is possible to perform multiple cycles in succession. When multiple cycles are performed, the residual vapor is represented by the equation:

$$R = 100 \cdot \left(\frac{P_{lo}}{P_{hi}}\right)^n \quad (2)$$

where n is the number of cycles. As is readily seen, the lower the pressure, the more pressurization-venting cycles are required in order to reduce the value of R (i.e., increase the amount of vapor extracted) to a particular desired value.

Typically a processor 70 automatically controls the amount of pressurization-venting cycles that are performed. Accordingly, an operator of the system 10 can determine how many cycles are desired by deciding upon an appropriate balance between the amount of vapor to be extracted and the amount of time to be expended performing additional cycles, and the operator can then input this value to the processor 70. Alternately, the operator can determine what percentage of residual vapor (R) is acceptable and input this value to the processor 70, which can then calculate amount of pressurization-venting cycles required according to the following equation:

$$n = Int\left[\frac{\log\left(\frac{(100-R)}{100}\right)}{\log\left(\frac{P_{lo}}{P_{hi}}\right)} + 0.5\right] \quad (3)$$

Figure 7:
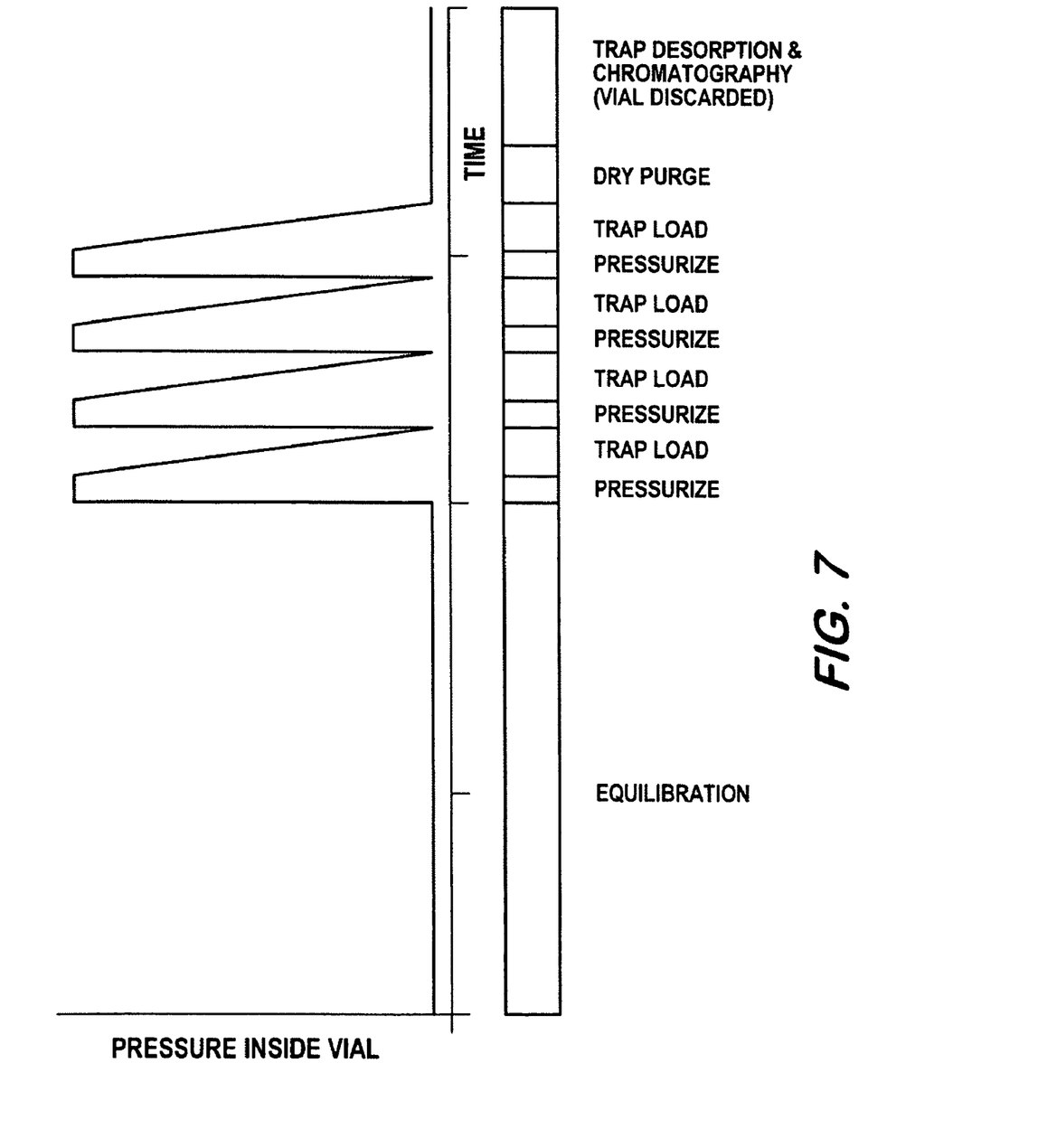
FIG. 7 is a plot of the pressure inside a headspace vial over time.

The number of pressurization-venting cycles input by the operator, or calculated by the processor 70, is then performed successively before the system 10 proceeds to perform the remaining steps discussed below. FIG. 8 illustrates a representation of the pressure inside the vial over time when multiple pressurization-venting cycles are employed.

Returning again to FIG. 3, in certain advantageous embodiments, the system 10 includes a gauge for determining the pressure in the headspace vial 20. Though this may be any device capable of measuring the pressure in the vial 20 and communicating this information to either the system or an operator of the system, in certain embodiments, this gauge is a pressure transducer 62 in fluid communication with the vial 20. Accordingly, as the carrier gas carrying the headspace vapor flows past the transducer 62, the operator may be promptly alerted upon detection of an undesirable condition in the vial 20 by, for example, an LED, an audible alarm, or a log report or profile on a visual display screen.

Because the rate of flow remains constant due to the use of the flow controller 72, various undesirable conditions can be easily detected by monitoring the pressure with the transducer 62, such as a leak in the vial, an incorrect starting pressure, an defective vial resulting in abnormal vial capacity, or the presence of too much or too little sample in the vial. As noted above, the drop in pressure is proportional to the amount of sample flowing out of the vial 20. Because vent time is normally proportional to both the sample volume in the vessel and the pressure, a plot of the pressure decay over time generally results in an exponential profile, making measurement and comparison of the pressure decays somewhat difficult. However, because the flow controller 72 maintains a constant flow rate, a plot of the pressure decay over time results in a linear profile. Therefore, measurement of the pressure decay is very useful in determining whether the vial has a leak or other undesired condition.

The system is first calibrated by obtaining a properly measured and sealed reference vial and running it on the headspace sampler. A number of readings of the pressure are taken at various points in time and stored in system memory for later comparison. Later, as each actual sample vial is tested, the same number of readings are taken and are subsequently compared to the corresponding values stored for the reference vial, and will check for any significant deviation. For example, the system may take twenty one readings for each of the reference vial and the sample vials, and then look for a deviation in the values of the sample vials of more than ten percent in three successive points from the reference vial. Values that are too high, for example, may indicate that too much sample may be present in the vial, while values that are too low may indicate that too little sample is in the vial or that the vial has a leak. If a deviation is found, the sample may be flagged in a system log or the operator may be otherwise alerted to the defective vial.

The transducer 62 may be located anywhere suitable for measuring the pressure prior to the influence of a flow controller. For example, as disclosed in FIG. 3, a transducer 64 may be positioned in the flow path immediately preceding the flow controller 72. However, in certain advantageous embodiments, a position proximate to the sampling head 24 is used, such as the position of pressure transducer 62 located at the needle purge 66, in order to avoid possible external factors from effecting an accurate measurement of the pressure, such as, for example, a slight pressure drop across the adsorbent 34.

Figure 4:
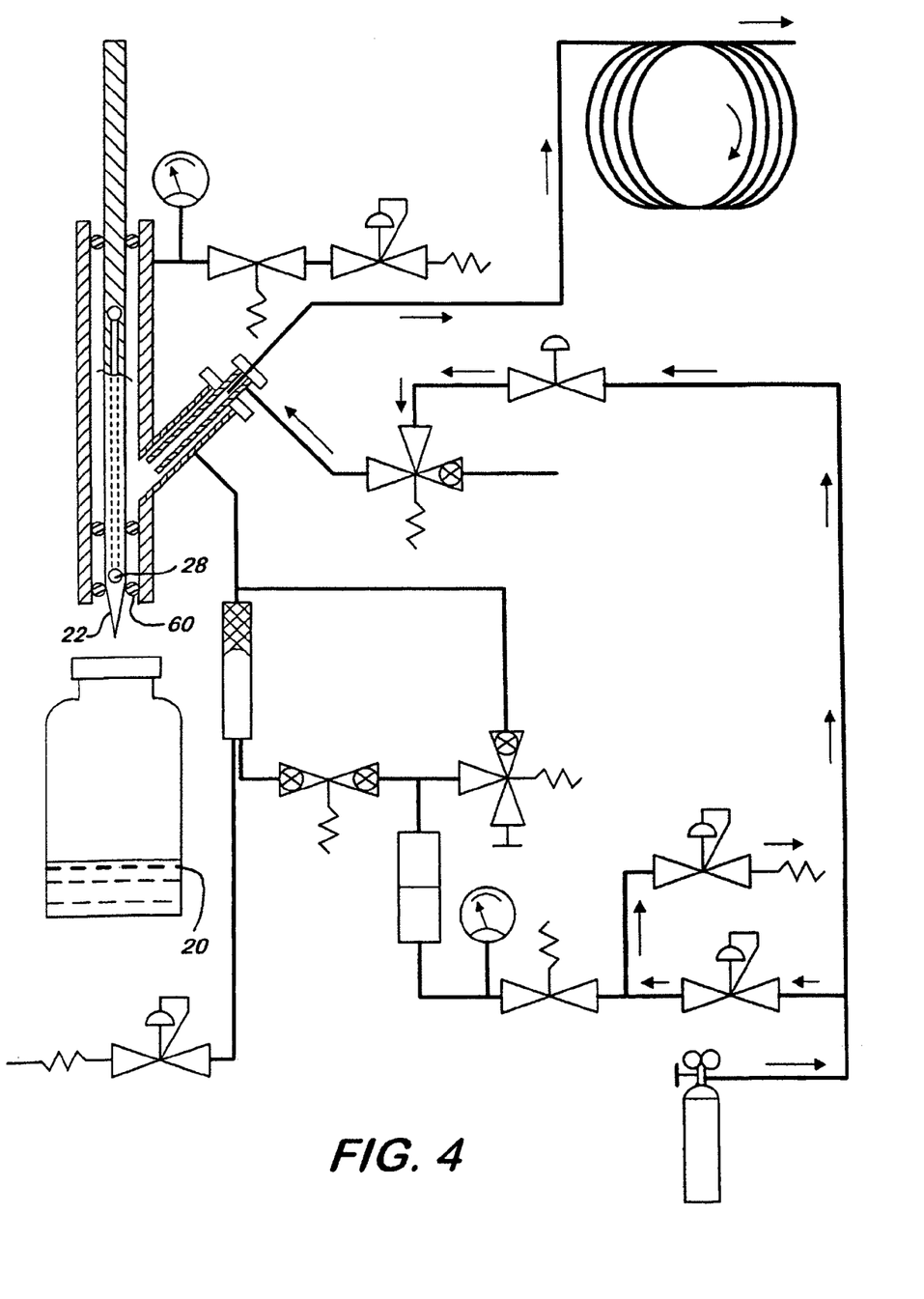
FIG. 4 is a schematic view of the system for extracting headspace vapor of FIG. 1 during the needle withdrawal stage.
Figure 5:
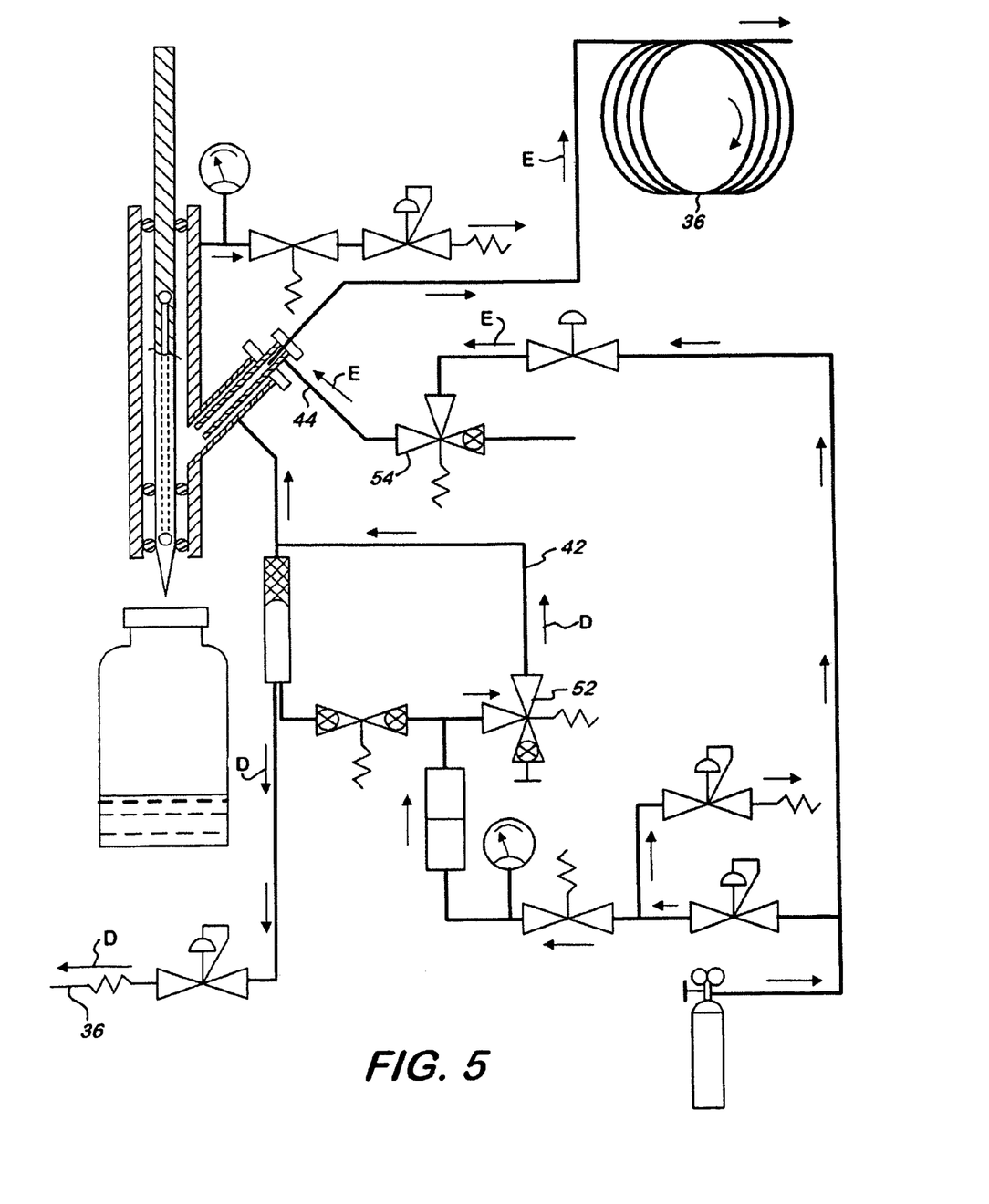
FIG. 5 is a schematic view of the system for extracting headspace vapor of FIG. 1 during the trap purge stage.

Next, in embodiments where a significant amount of moisture is present in the sample being analyzed, a dry purge step may be desired. As shown in FIG. 4, the needle 22 is first withdrawn from the vial 20, bringing the vessel port 28 above the seal 60. Next, as illustrated in FIG. 5, the inlet valve 52 is opened again, thereby allowing fluid to once again enter the system via the inlet 42. The fluid flows down into the adsorbent housing 32, sweeping any moisture therein out through the vent 36 (indicated by arrows D). Once again, the inlet valve 54 remains open, allowing fluid to continue to enter through the inlet 44 and isolate the column 36 (indicated by arrows E).

Figure 6:
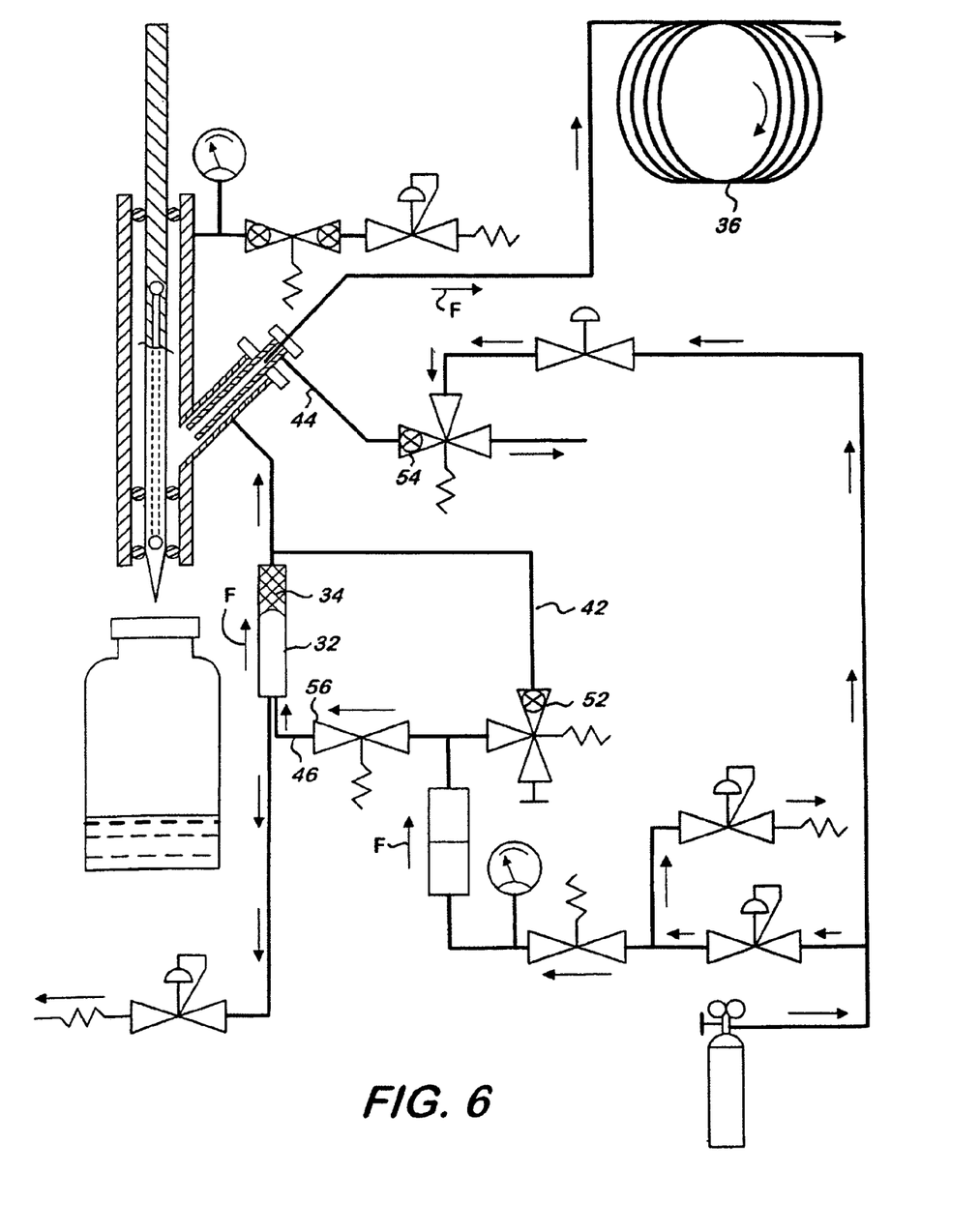
FIG. 6 is a schematic view of the system for extracting headspace vapor of FIG. 1 during the trap desorption stage.

A desorption step is illustrated in FIG. 6. As shown therein, the valves 52, 54 are closed, terminating the supply of fluid from inlets 42, 44. The valve 56 is opened, allowing fluid to flow in through inlet 46. The adsorbent housing 32 is heated to desorb the analytes retained by the adsorbent 34. Carrier gas enters through the inlet 46 and flows into the adsorbent housing 32, sweeping the desorbed analytes into the chromatographic column 36 (indicated by arrows F).

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of extracting headspace vapor, the method comprising the steps of:
   providing a vessel holding headspace vapor containing analytes to be measured;
   inserting a receptacle into the vessel;
   pressurizing the vessel by communicating carrier gas from a carrier gas inlet through the receptacle and into the vessel;
   venting the headspace vapor and carrier gas in the vessel through an adsorbent, which adsorbs analytes in the headspace vapor, and out a vent; and
   controlling the flow of the carrier gas and headspace vapor as they are vented such that the rate of flow is controlled to counter at least some of a decrease in pressure due to the depletion of headspace vapor in the vessel.

2. A method as claimed in claim 1, wherein the step of venting the headspace vapor and carrier gas comprises closing the carrier gas inlet.

3. A method as claimed in claim 1, further comprising the step of desorbing the analytes adsorbed by the adsorbent.

4. A method as claimed in claim 3, further comprising the step of purging the adsorbent of moisture by venting additional carrier gas through the adsorbent and out the vent prior to the step of desorbing the analytes.

5. A method as claimed in claim 1, wherein the step of controlling the flow comprises increasing the flow through a flow controller.

6. A method as claimed in claim 1, wherein the step of controlling the flow comprises maintaining a constant flow rate.

7. A method as claimed in claim 1, further comprising repeating the steps of pressurizing and venting a predetermined number of times.

8. A method as claimed in claim 7, wherein the steps of pressurizing and venting comprise a pressurization-venting cycle, the method further comprising the step of:
   determining the total number of pressurization-venting cycles to be performed; and
   wherein the predetermined number of times the steps of pressurizing and venting are repeated is one less than the determined total number of pressurization-venting cycles to be performed.

9. A method as claimed in claim 8, wherein the step of determining the total number of pressurization-venting cycles to be performed comprises the steps of:
   determining a percentage of the original headspace vapor to remain in the vessel as residual vapor; and
   calculating the number of pressurization-venting cycles required to extract enough of the original headspace vapor from the vessel such that the percentage of original headspace vapor remaining in the vessel after performing the calculated number of pressurization-venting cycles does not exceed the determined percentage.

10. A method as claimed in claim 9, wherein the number of pressurization-venting cycles required is calculated according to the equation:

$$n = Int\left[\frac{\log\left(\frac{(100-R)}{100}\right)}{\log\left(\frac{P_{lo}}{P_{hi}}\right)} + 0.5\right].$$

11. A method as claimed in claim 1, further comprising the step of monitoring the pressure in the vessel as the carrier gas carrying the headspace vapor is vented through the adsorbent and the vent to determine the rate of pressure decay in the monitored vessel.

12. A method as claimed in claim 11, further comprising the steps of:
   measuring the rate of pressure decay in a reference vessel to determine the rate of pressure decay therein;
   comparing the rate of pressure decay in the monitored vessel to the rate of pressure decay in the reference vessel to determine if the monitored vessel is defective.

13. A system for extracting headspace vapor, comprising:
   a vessel for holding headspace vapor containing analytes to be measured;
   a receptacle adapted to be inserted and withdrawn from said vessel, said receptacle having a vessel port;
   a carrier gas inlet for supplying carrier gas to pressurize said vessel and to carry the headspace vapor;
   an adsorbent housing in fluid communication with said carrier gas inlet, said adsorbent housing having an adsorbent disposed therein for adsorbing the analytes in the carrier gas carrying the headspace vapor;
   a vent in fluid communication with said adsorbent housing for venting the carrier gas carrying the headspace vapor;
   wherein, when the vessel port of said receptacle is in fluid communication with said vessel and said carrier gas inlet is open, carrier gas flows into and pressurizes said vessel;
   wherein, when the vessel port of said receptacle is in fluid communication with said vessel and said carrier gas inlet is closed, the headspace vapor and carrier gas flow into said adsorbent housing and are vented through said vent; and
   a flow controller in fluid communication with said adsorbent housing and said vent for controlling the rate of flow of the carrier gas and headspace vapor to counter at least some of a decrease in pressure due to depletion of the headspace vapor in said vessel.

14. A system as claimed in claim 13, wherein said flow controller is configured to increase the flow therethrough.

15. A system as claimed in claim 13, wherein said flow controller is configured to maintain a constant flow rate.

16. A system as claimed in claim 13, wherein said flow controller comprises a forward pressure regulator.

17. A system as claimed in claim 13, wherein said flow controller comprises a mass flow controller.

18. A system as claimed in claim 13, wherein said flow controller comprises an electronic flow controller.

19. A system as claimed in claim 13, further comprising a processor, wherein:
   the pressurization of said vessel and the venting of the headspace vapor and carrier gas through said vent comprise a pressurization-venting cycle;
   said processor is configured to receive data reflecting a number of pressurization-venting cycles; and
   said processor is configured to generate a signal causing the number of pressurization-venting cycles to be performed.

20. A system as claimed in claim 13, further comprising a processor, wherein:
   the pressurization of said vessel and the venting of the headspace vapor and carrier gas through said vent comprise a pressurization-venting cycle;
   said processor is configured to receive data reflecting a maximum percentage of the original headspace vapor in the vessel to remain as residual vapor;
   said processor is configured to calculate a number of pressurization-venting cycles required to extract enough headspace vapor from said vessel so as not to exceed the maximum percentage; and
   said processor is configured to generate a signal causing the calculated number of pressurization-venting cycles to be performed.

21. A system as claimed in claim 20, wherein said processor is configured to calculate the number of pressurization-venting cycles according to the equation:

$$n = Int\left[\frac{\log\left(\frac{(100-R)}{100}\right)}{\log\left(\frac{P_{lo}}{P_{hi}}\right)} + 0.5\right].$$

22. A system as claimed in claim 13, further comprising a gauge for monitoring the pressure in said vessel as headspace vapor flows out of said vessel.

23. A system as claimed in claim 22, wherein said gauge comprises a pressure transducer.

24. A method as claimed in claim 22, further comprising a memory for storing the rate of pressure decay in a reference vessel for later comparison with the rate of pressure decay in the monitored vessel to determine if the monitored vessel is defective.

25. A system as claimed in claim 13, wherein said adsorbent comprises carbon black.

26. A system as claimed in claim 13, wherein said adsorbent comprises a polymeric adsorbent.

27. A system as claimed in claim 13, wherein said adsorbent comprises a carbon molecular sieve.

* * * * *